US009243219B2

(12) United States Patent
Dimitrelos

(10) Patent No.: US 9,243,219 B2
(45) Date of Patent: Jan. 26, 2016

(54) SYSTEM AND METHOD FOR PRODUCING ALGAE

(71) Applicant: Geronimos Dimitrelos, Plantation, FL (US)

(72) Inventor: Geronimos Dimitrelos, Plantation, FL (US)

(*) Notice: Subject to any disclaimer, the term of this patent is extended or adjusted under 35 U.S.C. 154(b) by 210 days.

(21) Appl. No.: 13/647,559

(22) Filed: Oct. 9, 2012

(65) Prior Publication Data

US 2013/0244310 A1 Sep. 19, 2013

Related U.S. Application Data

(63) Continuation-in-part of application No. 13/423,735, filed on Mar. 19, 2012, now abandoned.

(51) Int. Cl.
| C12M 1/00 | (2006.01) |
| C12M 3/00 | (2006.01) |
| C12M 1/12 | (2006.01) |
| C12M 1/04 | (2006.01) |
| C12M 1/02 | (2006.01) |
| C12N 1/12 | (2006.01) |
| C12N 11/04 | (2006.01) |

(52) U.S. Cl.
CPC ............ *C12M 21/02* (2013.01); *C12M 23/06* (2013.01); *C12M 23/22* (2013.01); *C12M 23/58* (2013.01); *C12M 27/04* (2013.01); *C12M 31/02* (2013.01); *C12M 31/08* (2013.01); *C12M 31/10* (2013.01); *C12M 41/24* (2013.01); *C12N 1/12* (2013.01); *C12N 11/04* (2013.01)

(58) Field of Classification Search
CPC ...... C12M 21/02; C12M 27/00; C12M 27/02; C12M 31/10
USPC ........................................... 435/292
See application file for complete search history.

(56) References Cited

U.S. PATENT DOCUMENTS

| 2008/0087165 | A1* | 4/2008 | Wright et al. ............ 95/51 |
| 2009/0029445 | A1* | 1/2009 | Eckelberry et al. ...... 435/257.1 |
| 2009/0181438 | A1* | 7/2009 | Sayre .................. C10G 1/00 435/134 |
| 2009/0246863 | A1* | 10/2009 | Lin ................... 435/292.1 |
| 2010/0009335 | A1* | 1/2010 | Joseph et al. ............ 435/3 |
| 2010/0034050 | A1* | 2/2010 | Erb et al. ............. 366/342 |
| 2011/0281295 | A1* | 11/2011 | Sylvestre ............ C12M 21/02 435/29 |
| 2012/0045800 | A1* | 2/2012 | Hazlebeck .............. 435/134 |
| 2012/0240832 | A1* | 9/2012 | Hiatt et al. ............ 110/341 |
| 2012/0315692 | A1* | 12/2012 | Hu et al. ............. 435/292.1 |
| 2013/0045531 | A1* | 2/2013 | Weaver et al. ........... 435/292.1 |
| 2013/0078708 | A1* | 3/2013 | Roux Dit Buisson .... 435/257.1 |
| 2013/0149766 | A1* | 6/2013 | Beliaev et al. .......... 435/167 |

* cited by examiner

Primary Examiner — Nathan Bowers

(57) ABSTRACT

A system and method of growing and harvesting algae provided whereby the system encompasses incubation tanks, internal lighting, chilled air diffusers, and an inline incubation tank for continuous batch processing. A centrifuge separates algae from growth media, and the media is processed through a series of reclamation steps so that cleaned water is reused for fresh media.

21 Claims, 11 Drawing Sheets

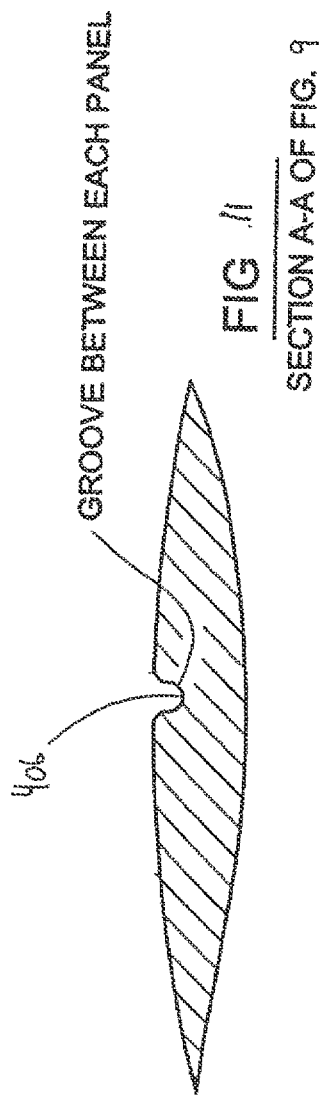

SYSTEM AND METHOD FOR PRODUCING ALGAE

CROSS-REFERENCE TO RELATED APPLICATION

This application is a continuation-in-part of U.S. patent application Ser. No. 13/423,735 filed on Mar. 9, 2012 entitled "A Comprehensive System and Method for Producing Algae," the contents of which are incorporated by reference herein.

FIELD OF THE INVENTION

The present invention relates to the field of algae harvesting and, more particularly, to an indoor system to efficiently grow and harvest algae and related methods.

BACKGROUND OF THE INVENTION

Many aspects of our current consumer- and producer-driven society have created the perception of a need for renewable and sustainable resources. Along these lines, it is recognized that algae can be grown and utilized as a human or animal food source. Algae are additionally used in the farming industry as a renewable source of fertilizer. Algae can also be used as an alternative to petroleum products, in the polymer and plastics industry, cosmetics industry, paint and die industry, as well as in the nutraceutical and pharmaceutical fields. There are known processes for growing and harvesting algae. However, many of these processes take a significant amount of time that do not provide for economic feasibility. It is therefore desired that a process be developed that optimizes growth and harvest time such that economic feasibility can be achieved.

SUMMARY OF THE INVENTION

The present invention is directed to a system for producing algae. In one embodiment, the system comprises an algae production tank for incubating algae in growth media and a light located inside the production tank capable of being submerged in the growth media. A rotating blade proximate the bottom of the production tank is placed for the purpose of mixing the growth media.

The system for producing algae, in another embodiment, comprises a substantially transparent cylinder that houses the light source to keep the light source dry and also to provide a route for cooled air to enter the cylinder and cool the lighting and media. The light is an LED, tubular skylight, fiber optic lighting, or any other lighting source known in the art.

The algae grown in the system is preferably at least one of *Haematococcus pluvialis*, *Chlorella zofingiensis*, and *Scenedesmus* species.

In an alternate embodiment, the system further comprises an air chiller that passes cooled air through the production tank for the purpose of cooling and aerating the growth media. A diffuser attached to the blade is connected to the chiller so that cooled air introduced into the diffuser is released from the diffuser and into the production tank to form a rotating curtain of air upon blade rotation.

An incubation tank is attached proximate the top of the production tank so that the contents of the incubation tank can pass through an opening and into the production tank.

A sheath substantially surrounds the production tank, thereby defining a space between the sheath and the production tank wherein cooled air exhausted from the production tank is allowed to pass into the space between the production tank and the sheath for externally cooling the production tank.

A centrifuge is connected to the production tank, and the algae in the growth media is introduced into the centrifuge to substantially separate the algae from the growth media supernatant.

In one embodiment, the system also comprises a water reclamation system comprising a particulate filter to filter particulate matter from growth media supernatant, a UV light source to kill living organisms, a reverse osmosis membrane, and gaseous ozone, wherein used growth media is cleaned and resulting cleaned water is utilized as a component of new growth media.

The invention also contemplates a method for producing algae comprising the steps of: incubating a first algae culture in a growth media within an incubation tank; transferring the first algae culture to a production tank having a greater capacity than the incubation tank; adding media to the production tank to increase the volume of media therein; increasing a cell density of the first culture in the production tank; incubating a second algae culture in a growth media within the incubation tank; transferring the second algae culture to the production tank; diffusing cooled air into the production tank; and providing a light source inside the production tank.

It is also contemplated that cooled air be exhausted from the production tank and directed proximate the incubation tank or proximate an exterior surface of the production tank.

In one embodiment, additional steps include transferring the media from the production tank to a centrifuge; and centrifuging the media to separate algae growing in the media from the media.

BRIEF DESCRIPTION OF THE DRAWINGS

For a fuller understanding of the invention, reference is made to the following detailed description, taken in connection with the accompanying drawings illustrating various embodiments of the present invention, in which:

FIG. 11 illustrates a side cutaway view of a portion of the bead in FIG. 9.

DETAILED DESCRIPTION OF THE INVENTION

In the Summary of the Invention above and in the Detailed Description of the Invention and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, that feature can also be used, to the extent possible, in combination with and/or in the context of other particular aspects and embodiments of the invention, and in the invention generally.

The term "comprises" is used herein to mean that other ingredients, elements, steps, etc. are optionally present. When reference is made herein to a method comprising two or more defined steps, the steps can be carried out in any order or simultaneously (except where the context excludes that possibility), and the method can include one or more steps which are carried out before any of the defined steps, between two of the defined steps, or after all of the defined steps (except where the context excludes that possibility).

In this section, the present invention will be described more fully with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will convey the scope of the invention to those skilled in the art.

The present invention relates to a combination batch and continuous system and related method for improved algae cultivation and subsequent processing.

Creating Starter Culture from Seed Culture

Figure 1:
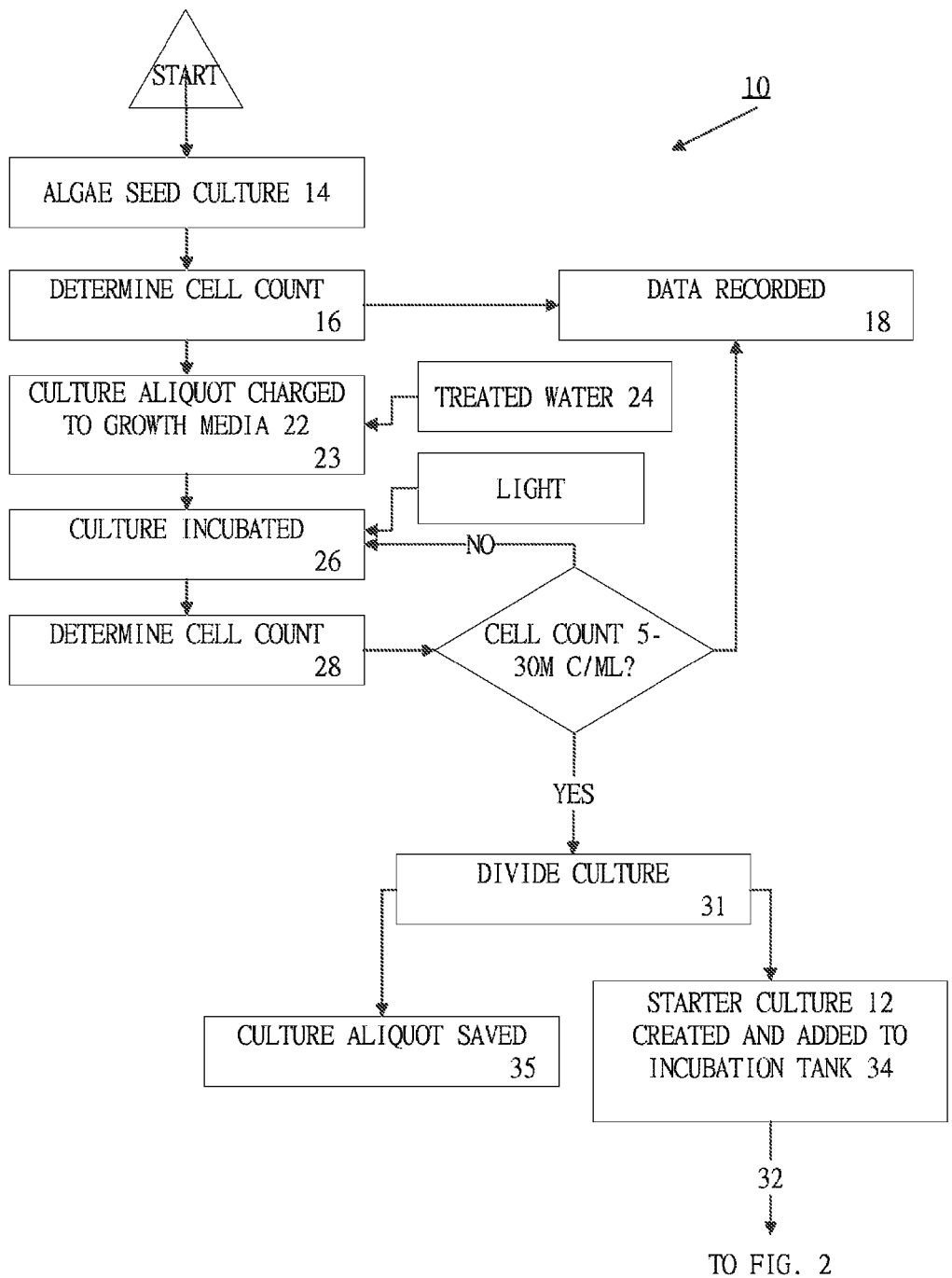
FIG. 1 is a flow chart showing the process to create a starter culture of the present invention.

Initially referring to FIG. 1, the method to grow algae begins with the creation 10 of a starter culture 12. The starter culture 12 is derived from algae seed cultures 14. Seed cultures 14 may be either from an outside source, such a frozen specimen ordered from an algae company, or prepared specifically for the process of the present invention. In one embodiment, the seed culture 14 is UTEX 2505 *Haematococcus pluvialis*.

In one embodiment, the process begins with identification of a particular culture, of which an accurate cell count is calculated in step 16 and recorded in step 18. An aliquot (i.e. a portion) of seed culture 14 is charged in step to an incubation vessel, such as an Erlenmeyer flask, containing growth media 22 and an appropriate volume of treated water 24. Water is treated with at least one of filtration, reverse osmosis, distillation, deionization, and ultraviolet light. As a non-limiting example of an embodiment of the present invention, one hundred milliliters of a ten percent culture are charged to a one liter flask, and 600 ml of purified water and the appropriate nutrients are added. A commercially available nutrient product containing nitrate, phosphate, and trace minerals is used along with a B-vitamin complex mix. A culture pH is maintained at about 7.2 to about 7.5.

The culture is incubated in step 26 and allowed to multiply to a desired cell density. The desired cell density is between about 1M cell/ml and about 30M cells/ml, depending on the particular culture. For example, *Haematococcus pluvialis* is incubated to reach a density of about 1M cells/ml to about 6M cells/ml. *Chlorella zofingiensis* is incubated to reach a density of about 6M cells/ml to about 21M cells/ml. Mixed *Scenedesmus* species is incubated to reach a density of about 9M cells/ml to about 30M cells/ml. Mixed cultures are incubated to reach a density of about 6M cells/ml to about 15M cells/ml.

Figure 2:
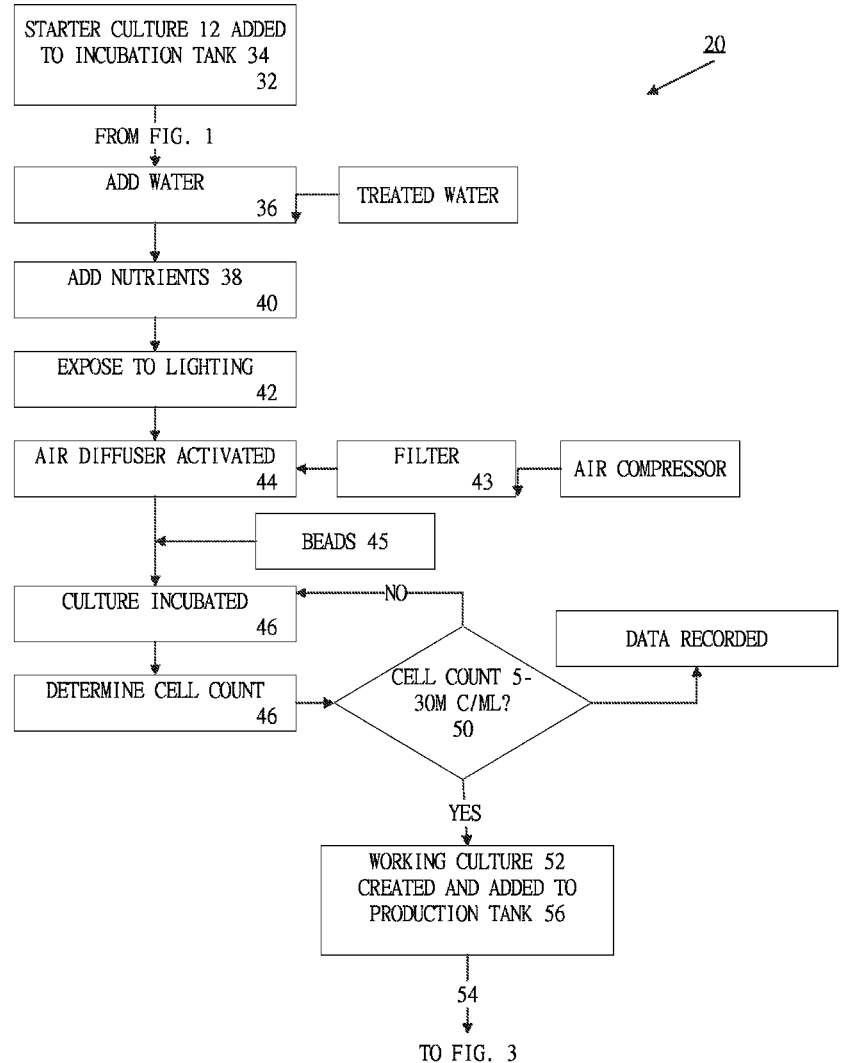
FIG. 2 is a flow chart showing the process to create a working culture of the present invention.

With continuing reference to FIG. 1, once the cell count determined in step 28 and the cell density is within the desired range of 1-30M cells/ml (depending on algae strain), the culture, which is now considered the "starter culture" 12, is then transferred in step 32 to an incubation tank 34 (FIG. 2).

The incubation tank 34 volume ranges from about 100 L to 800 L. In an example of one embodiment, the incubation tank 34 is about a 230 liter tank.

In one embodiment, when transferring starter culture 12 to the incubation tank 34, the culture is divided in step 31 so that about 90% of the starter culture 12 is transferred in step 32 to the incubation tank 34, and the remainder of the culture is saved 35 and used as seed culture 14.

Creating Working Culture from Starter Culture

With reference to FIG. 2, water is added in step 36 to the incubation tank 34. Nutrients 38 that support algae proliferation are also added in step 40 to the incubation tank 34. The culture in the incubation tank 34 is then exposed to lighting in step 42. The incubation tank 34 is constructed and arranged to expose the culture to a light source. This occurs through the use of at least one of incandescent lighting, fluorescent lighting, tubular skylight, fiber optic cables that channel sunlight, and LED lighting.

Compressed air subject to filtration in step 43, and the air is introduced into the tank 34. In one embodiment, air is chilled to combat relatively warm ambient temperatures. In particular, compressed air introduced to the tank should be between about 72° F. and 87° F., and preferably between 75° F. and 81° F. In an environment where the ambient temperature is below 70° F., air of ambient temperature is used, since heat from lighting systems is sufficient to keep the culture within desired temperature ranges. In one embodiment, the compressed air is filtered in step 43 through sub-micron filtration system.

The culture is incubated in step 46 and allowed to multiply to a desired cell density. The appropriate cell density is between about 1M cell/ml and about 30M cells/ml, depending on the particular culture. For example, *Haematococcus pluvialis*, is incubated to reach a density of about 1M cells/ml to about 6M cells/ml, *Chlorella zofingiensis*, is incubated to reach a density of about 6M cells/ml to about 21M cells/ml, and the mixed *Scenedesmus* species is incubated to reach a density of about 9M cells/ml to about 30M cells/ml, and mixed cultures are incubated to reach a density of about 6M cells/ml to about 15M cells/ml.

In one embodiment, beads 45 are added to the culture to promote algae growth and to maintain the system in a clean state by reducing algae adherence to internal system surfaces.

With continuing reference to FIG. 2, once the cell count is determined in step 48 and the cell density is within the desired range 50, the culture, which is now considered the "working culture" 52, is then transferred in step 54 to a production tank 56. The production tank 56 volume ranges from about 6,000 L to 15,000 L. In an example of one embodiment, the incubation tank is about a 11,500 liter tank.

Figure 3:
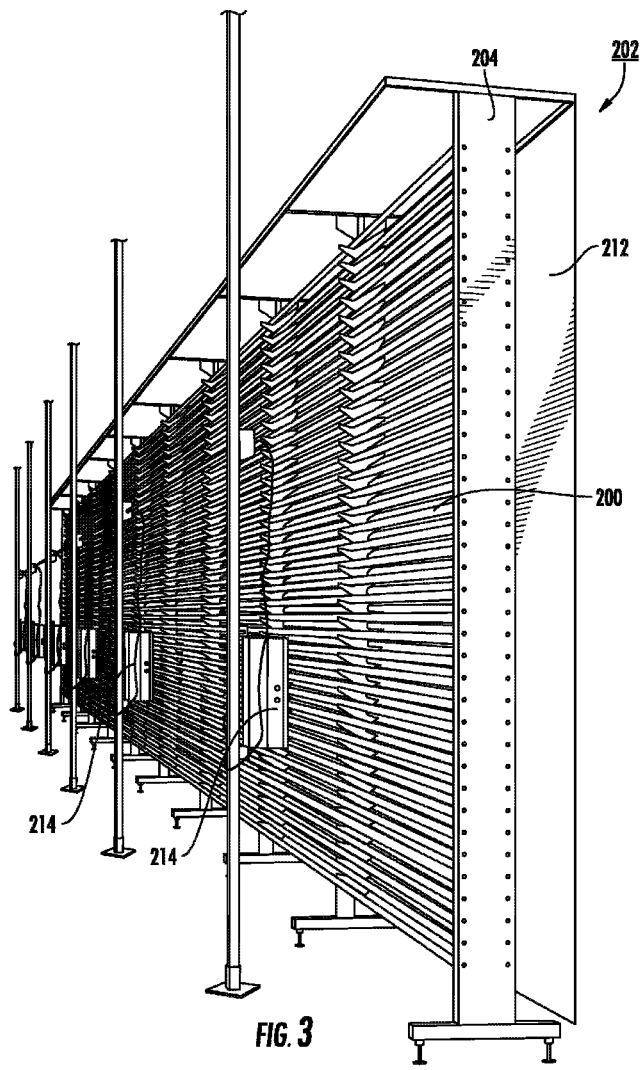
FIG. 3 illustrates perspective view of an embodiment of an incubation vessel.
Figure 4:
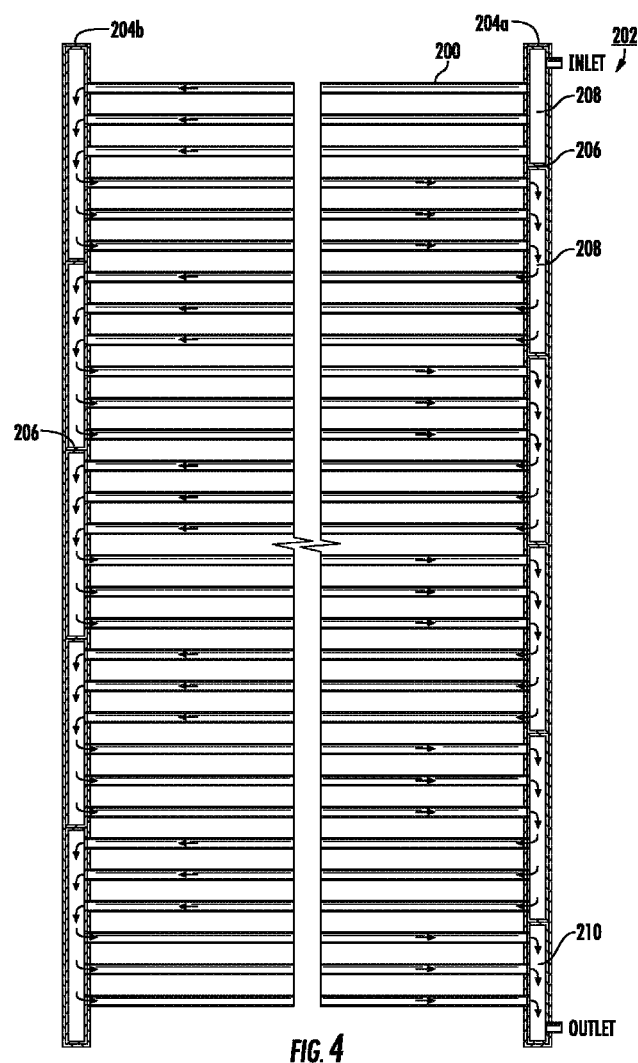
FIG. 4 illustrates a side cutaway view of the incubation vessel of FIG. 3.

Turning to FIGS. 3 and 4, in one embodiment, the incubation tank 34 is a series of transparent tubes 200 configured to form a "light fence" 202. In this configuration, substantially hollow end posts 204 are connected to each other via a plurality of hollow transparent tubes 200. Each tube 200 sealedly connects to each end post 204. Baffles 206 within each end post are situated periodically to create individual liquid-proof chambers 208 within each post. Media introduced into the top of a first post 204a travels through a tube to a second end post 204b to fill a baffled chamber 208 in the second end post 204b. Additional tubes 200 are installed in the posts 204, 204a, 204b, so that media that travels from the first post 204a to the second post 204b enters a lower tube and travels back to a second, lower, baffled chamber in the first post 204a. This pattern repeats itself, back and forth, until media travels through multiple tubes 200 and multiple baffled compartments 208 until the media reaches a final chamber 210, wherein a pump recalculates the media to the top baffle of the first post 204a so that the media may travel through the light fence 202 again.

This configuration provides a reflective surface 212, such as a mirror or Mylar (Biaxially-oriented polyethylene terephthalate) film, to be situated on one side of the fence, while at least one light source 214 is situated on the opposing side. This allows light to directly hit the tubes 200 from one side (where the light source resides), and for reflected light that strikes the reflective surface 212 and illuminates the opposing sides of the tubes 200.

Production Process

Figure 5:
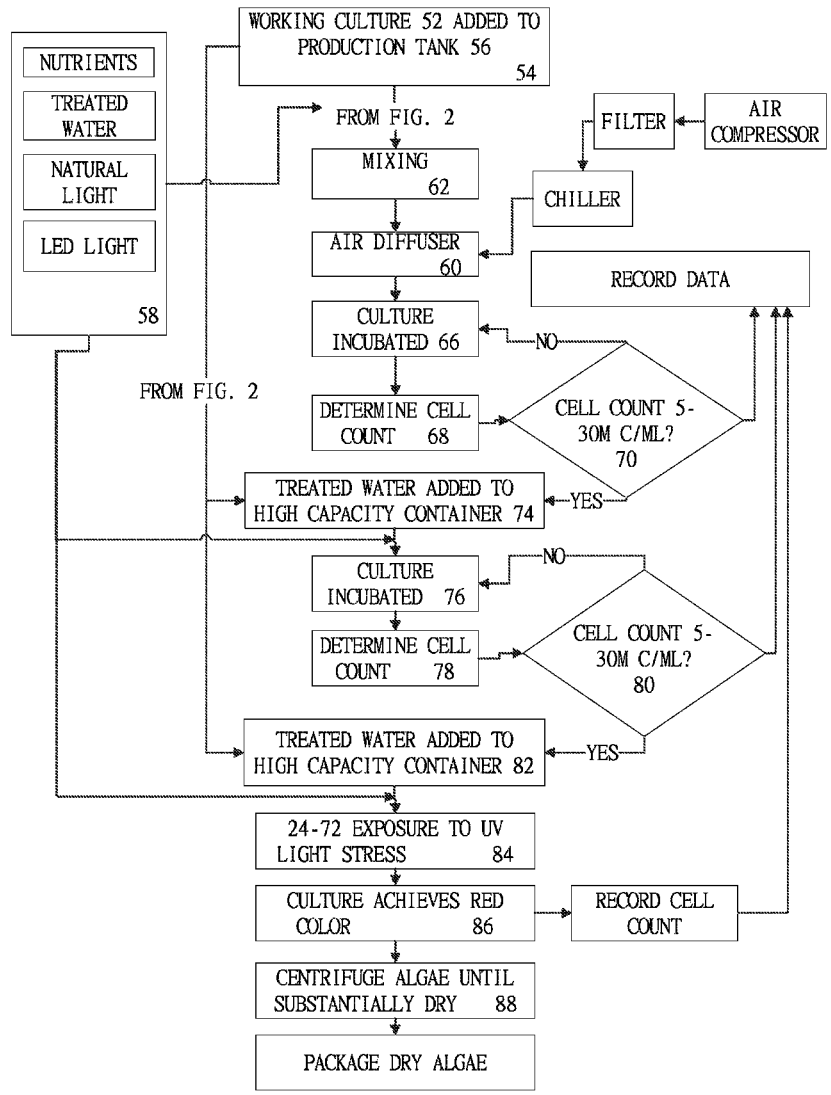
FIG. 5 is a flow chart showing the production process of the present invention.

Turning to FIG. 5, in one embodiment, the working culture 52 is added in step 54 to the production tank 56. In a preferred embodiment, approximately 3,300 L of water are added along with nutrients and light exposure 58. At this point in the process, the culture is referred to as the production culture. It should be noted that the transfer of culture between tanks is a point of potential contamination, for open air exposure of culture leaves the culture vulnerable to exogenous pathogens and contaminating organisms. The present invention reduces or eliminates such contamination opportunities by installing the incubation tank 34 directly above the production tank 56.

Figure 6:
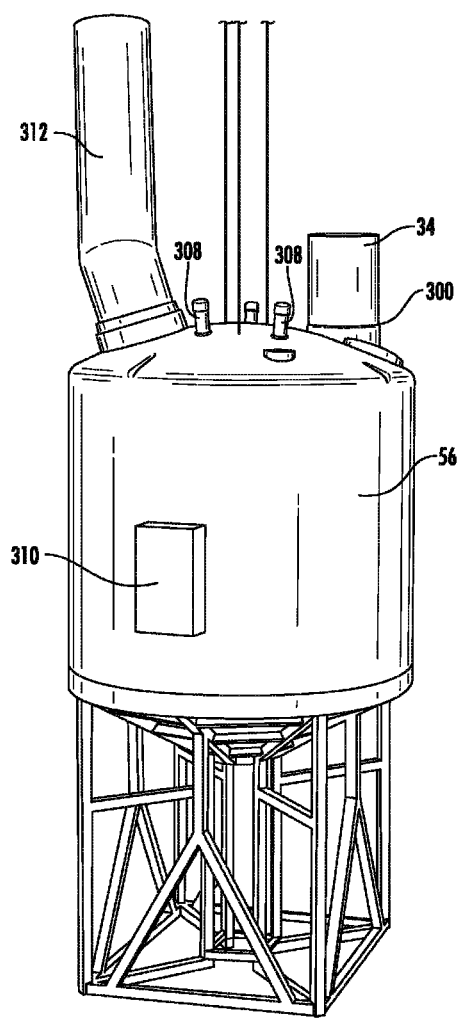
FIG. 6 illustrates a perspective view of a production tank.

FIG. 6 illustrates, inter alia, the incubation tank 34 directly above the production tank 56. A solenoid-controlled junction, door, valve, or other controlling means in association with the incubation tank 34 allows the working culture in the incubation tank 34 to be emptied into the production tank 56. The junction 300 between these two tanks is sealed from the environment, thereby essentially eliminating a primary contamination opportunity. This also allows the production flow to be a combination of continuous and batch processing. Batches of working culture 52 can be made in batch, while the culture in the production tank 56 is continually grown.

Turning again to FIG. 5, Air is introduced to the production culture in step 60 in a manner similar to the manner described above relating to the process to create the starting culture 12. In one embodiment, chilled compressed air is gently diffused through tubes that feed into at least one of an aeration hose, diffuser bar, or diffuser grid.

Figure 7:
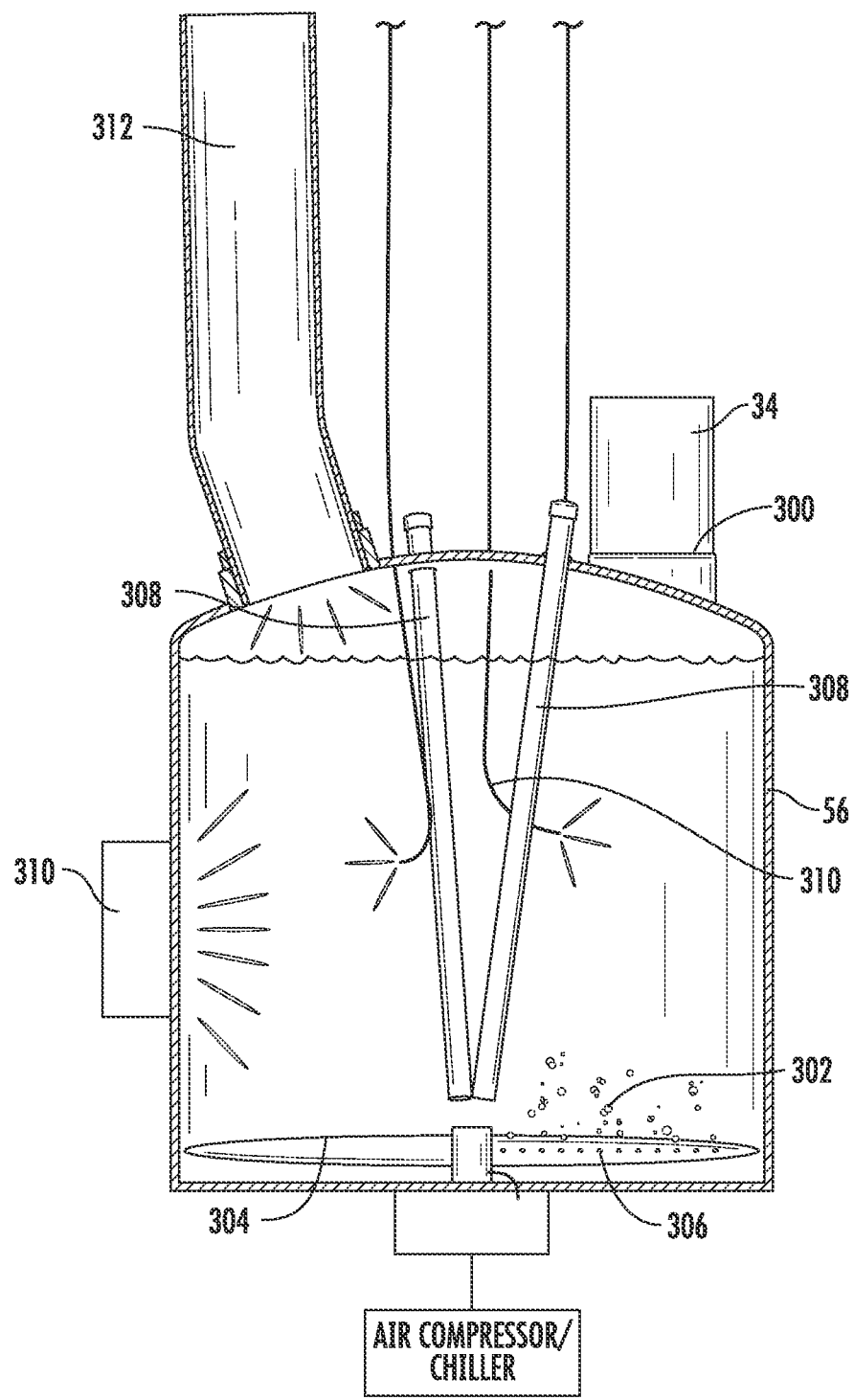
FIG. 7 illustrates a side cutaway view of the production tank of FIG. 6.

With reference to both FIGS. 5 and 7, the present invention incorporates a combination of airlifting in bubble columns 302 combined with propeller 304 mixing in step 62. Such mixing in step 62 allows the algae to evenly flow throughout the tank to absorb nutrients and light. If the algae are mixed too fast, it will cause sheer stress and damage the algae. If it is mixed too slow, algae will sink and not be able to receive light or nutrients. Bubble columns 302 alone provide efficacious mixing, but to mix properly necessitates the introduction of large amounts of air which causes sparger death. Using a propeller 304 or a pump alone to mix the algae causes shear stress and death due to the high rotational speed required to provide appropriate levels of mixing.

In a preferred embodiment, an algae mixing propeller 304 rotates between about 6 and about 15 rpm. A gear motor, rotary coupling, and chain and sprocket keep the propeller 304 rotating, but any propeller-rotation mechanism known in the art is contemplated. Additionally, an air diffusing conduit 306 runs substantially the length of a blade in order to concurrently mix the culture while bubble columns 304 originating from the blade provides an airlifting action. This reduces or eliminates both excessive shear stress and sparger death.

Returning to FIG. 5, it should be noted that when transferring the working culture 52 to the production tank 56 in step 54, mixing must continue to prevent the algae from sinking to the bottom of the tank 56.

The culture is incubated in step 66 and allowed to multiply to a desired cell density as previously described herein. The pH is maintained between about 7.2 and about 7.5. Once the cell count is determined in step 68 and the cell density is within the desired range 70, additional water is added in step 74 to the production tank 56. In a preferred embodiment, approximately 200 L additional working culture 52 and approximately 3,300 L of additional water are added in step 74 to the production tank 56 along with additional nutrients and continuing light exposure 58.

With continuing reference to FIG. 5, the culture is once again incubated in step 76 and allowed to multiply to the desired cell density as previously described herein. The pH is maintained between about 7.2 and about 7.5. Once the cell count is again determined in step 78 and the cell density is within the desired range 80, additional culture is added 72 and additional water is added 82 to the production tank 56. In a preferred embodiment, approximately 200 L additional working culture 52 and approximately 3,300 L of additional water are added in step 82 to the production tank 56 along with additional nutrients and continuing light exposure 58.

Prior to harvest the algae culture is stressed. In particular, nutrients are withheld and additional water is added. The culture is additionally exposed to ultraviolet light in step 84. The production tanks 56 utilize the same lighting scheme as the incubation tanks 34 until the culture is to be stressed to promote lipid and astaxanthin synthesis. The culture is exposed to both UVA and UVB light in order to stress the algae. In a preferred embodiment, the UV spectrum is about 210 nm to about 400 nm. Concurrent with non-UV light, a portion of the total light utilized comprises light in the UV spectrum, to which the culture is exposed for between about 24 hours and 72 hours, or until the culture turns the color red in step 86.

Algae Isolation

Once the culture is red, algae are harvested using centrifuge 88 at about 4200 rpm for about 3 hours before algae are removed. In one example, the algae are passed through an Evodos centrifuge system to de-water the algae. To save water, the supernatant 89 (FIG. 8) is sanitized and used to make fresh media.

The supernatant is passed through at least one of an about 1 to about 3 micron filtering system, UV light, ultra filtration, reverse osmosis membranes, and a holding tank with bubbling ozonation before the purified supernatant (water) is returned to the production tank 56. In one embodiment, the production tank 56 also has the means to ozonate the fluid held therein.

Figure 8:
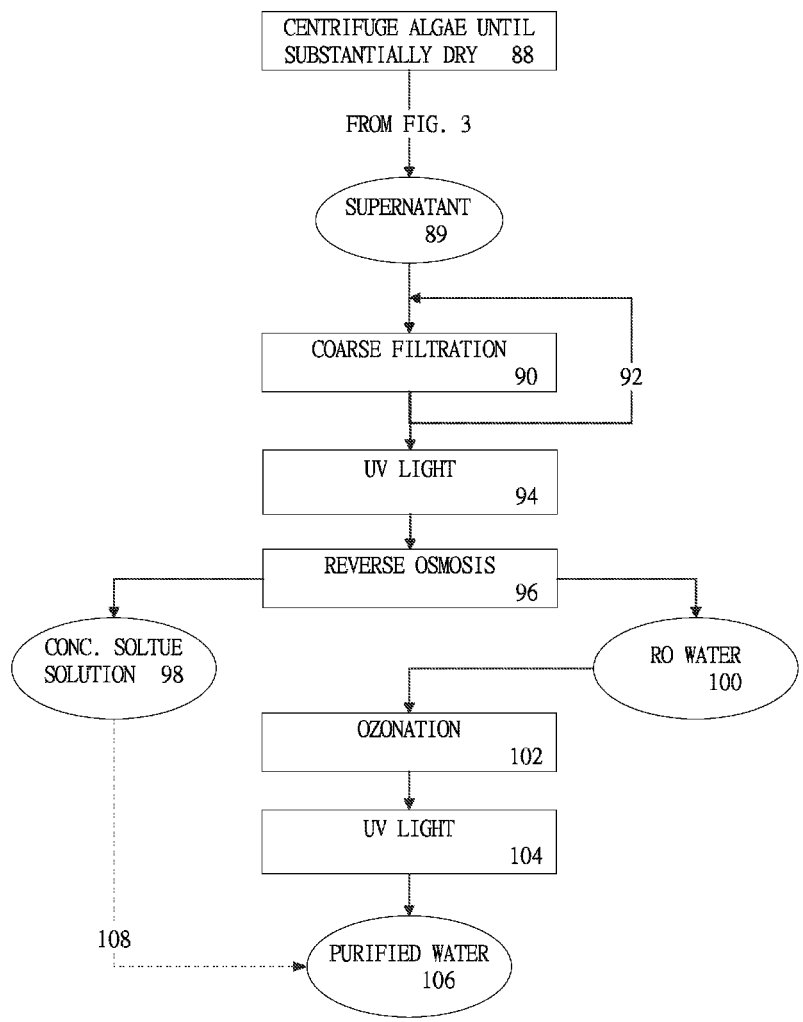
FIG. 8 is a flow chart showing the centrifugation and water reclamation process of the present invention.

With reference to FIG. 8, after the algae are substantially removed from the media in the centrifuge in step 88, the supernatant 89 is filtered through a relatively coarse mechanical filter in step 90, such as an about 4 micron to about 10 micron bag filter. This process may be repeated as in step 92. The filtered supernatant 89 is exposed to UV light in step 94 to promote the killing of any living matter. The supernatant 89 is then passed through a reverse osmosis filtration system in step 96, resulting in a concentrated solute solution 98 and reverse osmosis (RO) water 100.

With continuing reference to FIG. 8, ozone is introduced into the RO water in step 102. Ozone is a pungent, naturally-occurring gas possessing strong oxidizing properties, and has a long history of safe use in disinfecting water sources. Ozone rapidly attacks bacterial cell walls and is generally thought to be a more effective anti-pathogenic agent than chlorine. Ozone is reported to have 1.5 times the oxidizing potential of chlorine, yet contact times for this antimicrobial action are typically 4-5 times less than that of chlorine, all without the unwanted byproducts associated with chlorine.

Ozone cannot be stored and transported like most other industrial gases, so must therefore be locally produced. Ozone can be produced in a number of ways known in the art. The most common methods are by the use of UV light and coronal discharge.

A UV lamp emitting light at approximately 185 nm in the presences of air (which is approximately 21% oxygen) will cause some diatomic oxygen ($O_2$) molecules to split, resulting in single oxygen atoms ($O^-$) that bind to other diatomic oxygen molecules to form ozone ($O_3$). The coronal discharge method of ozone is employed for many industrial and personal uses. While multiple variations of the "hot spark" coronal discharge method of ozone production exist, these units usually work by means of a coronal discharge tube. Coronal discharge tubes are typically cost-effective and do not require an oxygen source other than the ambient air to produce ozone. In one embodiment of the invention, ozone is generated with a corona discharge device. In such a device, air passes through an electrical field wherein ozone is generated.

After ozone is introduced into the water in step 102, the water is exposed a second time to UV light in step 104 for antimicrobial purposes and also to expedite the degradation of ozone so that algae may be reintroduced to this purified water 106 for growing subsequent cultures. The concentrated solute solution 98 may be partially re-introduced in step 108 into this culture to balance ion concentrations.

Water sent into the production tank 56 is fed through a sprinkler system in order to rinse and sanitize all parts of the tank. The sprinkler sprays water in a substantially circular pattern within the production tank 56 to rinse all inside surface area of the production tank 56.

Beads

In a preferred embodiment of the present invention a cell growth culture is initiated on a relatively small scale 23 in which beads 45 are placed within the vessels growing culture. It has been surprising to find that the presence of the beads 45 provide between about a five to thirty percent accelerated growth of algae within a three day time period of beads 45 and nutrient being added to the flask. Beads 45 placed in the growing culture also ricochet off of internal surfaces of the system and reduce the adherence of algae to these surfaces.

In one embodiment, the beads 45 are made from a substantially inert material. Polymer or plastic beads 45 are formed such as through injection molding or any other process known in the art. The beads 45 are either hollow or solid. The beads 45 are constructed to have a density that prevents the beads 45 from either sinking to the bottom of a culture vessel or from floating to the top of a culture vessel. The beads 45 may be porous to promote algae growth within the beads. In this case, the beads 45 can be used to seed larger cultures with cells that occupy the beads 45. In another embodiment, a mix of beads with differing densities are used to provide a bead mixture wherein the distribution of beads floating in solution ranges from beads floating near the top of solution to beads sinking to near the bottom of solution, and beads in between these extremes.

In another embodiment, the beads 45 are made from materials having properties advantageous to the media, such as sodium alginate. For example, the beads 45 may comprise reagents to buffer the pH of the solution and/or provide nutrients for the algae. In a related embodiment, algae are embedded in beads and aid in seeding the culture when exposed to media. Beads may be inert with an active coating or a pellet containing any desired nutrient or chemical compound known in the art. Beads 45 that are made from active compounds are, in another embodiment, capable of dissolving over time in solution.

Beads 45 are opaque, transparent, or translucent, and are reflective in some embodiments. The size of beads 45 ranges from about 3 mm in diameter to about 9 mm in diameter, with a preferred size being about 6 mm in diameter. The shape of the beads is substantially spheroid. In another embodiment, the beads are substantially polyhedral. The surface is smooth, rough, or ribbed.

Figure 9:
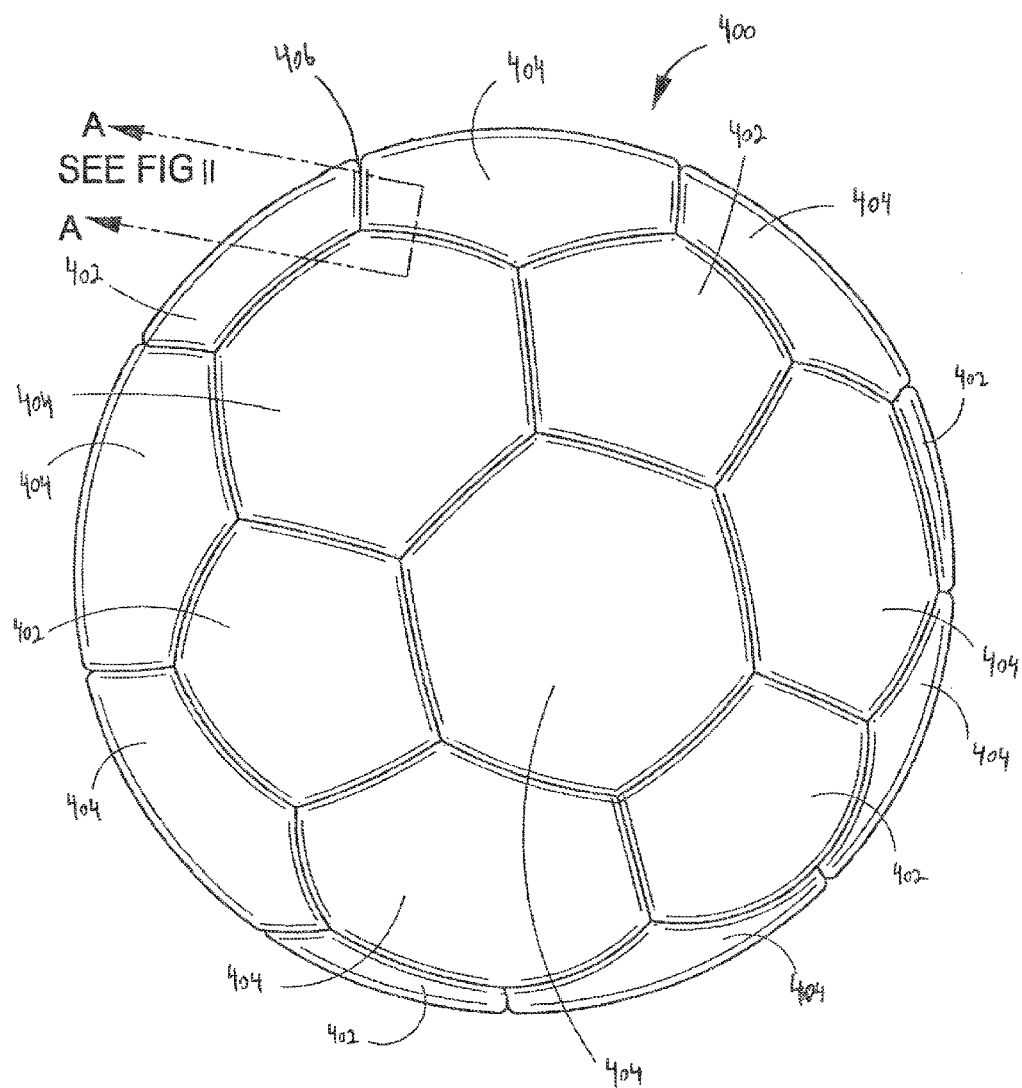
FIG. 9 illustrates a side view of a bead.

Referring initially to FIG. 9, in a preferred embodiment, the beads 400 are formed into a truncated icosahedron comprising a plurality of pentagonal 402 and hexagonal 404 panels. In particular, each pentagonal panel 402 is bordered by five hexagonal 404 panels. In one embodiment a spherical polyhedron is formed by configuring each panel to form a convex surface.

Figure 10:
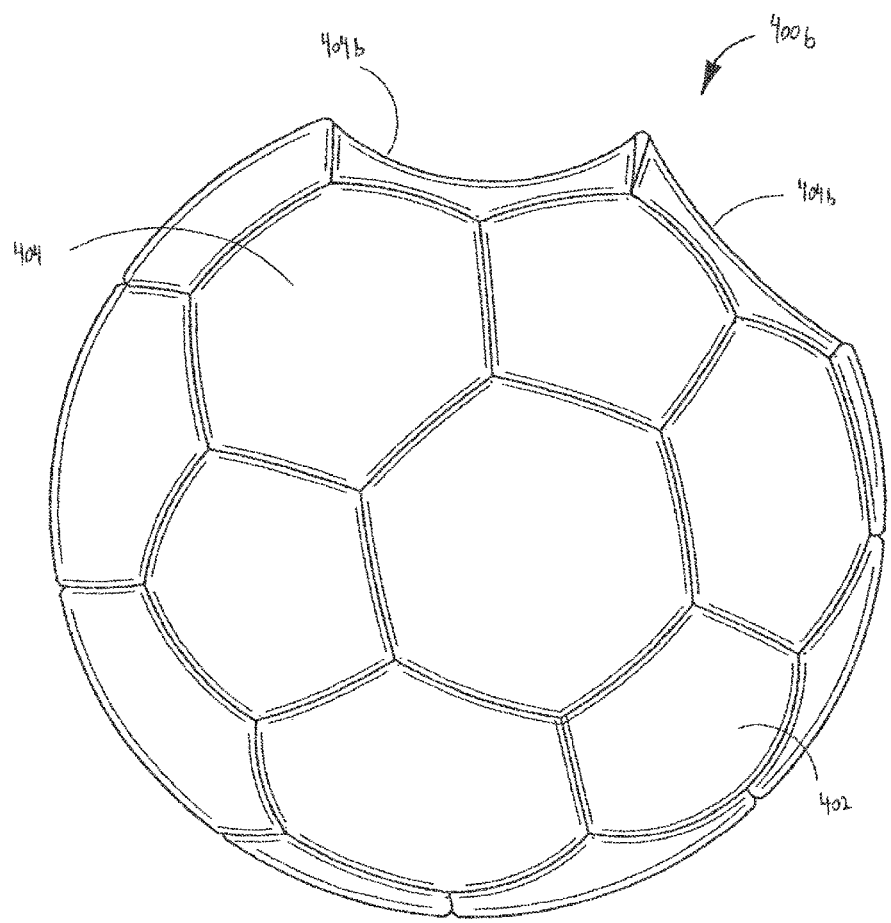
FIG. 10 illustrates a side view of an alternate embodiment of a bead.

FIG. 10 illustrates yet another embodiment of a bead 400b wherein at least one panel of the bead 400b is configured to have a concave surface 404b so that currents and ricochet forces do not result in a regular or repeating angle of deflection off of surfaces.

FIGS. 9 and 11 illustrate grooved junctions 406 where the panels 402, 404, 404a meet adjacent panels 402, 404, 404a. In another embodiment, the junctions are raised instead of grooved.

Air and Media Cooling

As shown in FIG. 5, the air introduced 60 to the production culture is chilled prior to entry. This cools the culture from the core as opposed to trying to keep the environment chilled, which is more controllable, and less costly. Air is filtered prior to entry into the culture to prevent contamination. Cooling is accomplished by at least one of heat plate exchangers, peltier coolers, radiators, heat sinks, absorption liquid chillers, centrifugal liquid cooled chillers, compressor chillers, helical rotary HVAC liquid chillers, scroll air-cooled chiller systems, cooling towers, and any other active or passive air chilling means known in the art.

The chilled air introduced into the production tank 56 is exhausted from the tank 56, yet still possesses cooling properties, so the exhausted air is directed proximate the incubation tank 34 to reduce the temperature of the working culture 52. In one embodiment, the exhausted air is guided through the working culture 52 to reduce the core temperature of that solution. In either case, this air, which is still relatively chilled, is guided through a duct system to finally exhaust into a sheath that covers the production tank 56. This sheath is preferably made from a reflective material so that it reflects lights installed externally to the production tank 56 back to the tank 56, but also creates a substantially cylindrical duct that envelopes the production tank and cools the lights and exterior surface of the tank as a penultimate use of the chilled air before it is exhausted to generally cool the production environment. This obviates the need to mist the tanks with water, thereby saving money and preventing the use of a relatively messy practice that increases the potential for contamination.

Lighting

As shown in FIGS. 3, 6, and 7, to lower electricity needs and provide the full natural spectrum of visible light to a culture, fiber optic cabling that channels natural sunlight to the incubation tank 34 is utilized in conjunction with LED lighting to promote algae growth. It has been discovered that a combination of ambient light provided through fiber optic cables and skylights as well as light provided by light emitting diodes (LEDs) significantly accelerates the growth rate of algae when compared to ambient light alone.

In a preferred embodiment, LumiGrow ES330 LED Grow Lights and Parans SP3 fiber optic natural lighting are used to provide light to the maintenance of seed cultures 14 and starter cultures 10. Other branded or generic LED grow lights are also contemplated. During the day, the Parans lighting provides natural daylight (about 380 nm to about 750 nm) and at night the Lumigrow lighting provides artificial light (about 420 nm to about 720 nm). The light/dark cycle for a given 24 hour period is about 8 hours light, about 4 hours dark, about 8 hours light, about 4 hours dark. For example, approximately 8 hours of sunlight is followed by 4 hours of resting dark, which is followed by 8 hours of LED light, finishing with 4 hours of resting dark. The LED lighting, however, may also be provided in conjunction with sunlight. The wavelength of the Parans light is about 400 nm to about 730 nm.

The various culture vessels used throughout the algae growing process may comprise (or be situated near) a LumiBar LED Strip Light, Parans SP3 fiber optic natural light and Caberra G2 ActiveLED-Growbar. The LumiBar and Parans both emit similar spectra (about 400 nm to about 730 nm). The Caberra G2 emits about 390 nm to about 780 nm spectrum of light. Similar LED light apparatuses and configurations are also contemplated.

With continuing reference to FIGS. 5-7, the production tank 56 comprises transparent cylinders 308 that project into the interior portion of the tank 56. The cylinders 308 contain LED lights and provide light deep within the culture solution in addition to external sources of light 310, as each cylinder 308 is submersed into the media. To keep temperatures regulated, the cylinders 308 receive cooled air proximate their bottom regions, and this air is exhausted out of the cylinders proximate their top regions.

In a similar manner to the submerged lighting cylinders, fiber optic conduits 310 that deliver sunlight, such as the Parans systems described herein, are also submerged in the media to provide sunlight deep within the production tanks 56. A tubular skylight 312 also directs light into the production tank 56.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

What is claimed is:

1. A system for producing algae comprising:
an algae production tank having algae growth media therein; a light located inside the production tank, the light capable of being submerged in the growth media; a rotating blade proximate a bottom of the production tank for the purpose of mixing the growth media; and, wherein the system further comprises a plurality of beads in the growth media to limit algae growth on interior surfaces of the tank, light and blade and to provide accelerated algae growth, wherein the beads are porous to promote algae growth within the beads, and wherein at least one panel of the bead is configured to have at least one concave surface so that current from the mixing of the growth media does not result in a repeating angle of deflection of the beads.

2. The system for producing algae of claim 1 further comprising a substantially transparent cylinder that houses the light source.

3. The system for producing algae of claim 1 wherein the light is an LED.

4. The system for producing algae of claim 3 wherein the LED produces light in the spectrum from about 380 nm to about 750 nm.

5. The system for producing algae of claim 3 wherein the LED produces light in the ultraviolet spectrum.

6. The system for producing algae of claim 1 comprising a tubular skylight connected to the production tank to divert sunlight into the production tank.

7. The system for producing algae of claim 1 wherein the light is fiber optic lighting that transmits sunlight to the interior of the production tank.

8. A system for producing algae of claim 1, wherein the algae is at least one of *Haematococcus pluvialis, Chlorella zofingiensis*, and *Scenedesmus* species.

9. The system for producing algae of claim 1, further comprising an air chiller that passes cooled air through the production tank for the purpose of cooling and aerating the growth media.

10. The system for producing algae of claim 9 further comprising a diffuser attached to the blade, the diffuser connected to the chiller so that cooled air introduced into the diffuser is released from the diffuser into the production tank to form a rotating curtain of air upon blade rotation.

11. The system for producing algae of claim 9 wherein the cooled air is passed through the cylinder for the purpose of cooling the cylinder and light source.

12. The system for producing algae of claim 9 wherein a sheath substantially surrounding the production tank defining a space between the sheath and the production tank wherein cooled air exhausted from the production tank and into the space for externally cooling the production tank.

13. The system for producing algae of claim 1 further comprising an incubation tank attached proximate a top of the production tank, the incubation tank defining an opening whereby contents of the incubation tank can pass therethrough to the production tank.

14. The system for producing algae of claim 13 further comprising a junction between the incubation tank and the production tank that is sealed to prevent contaminants from entering the incubation tank and the production tank.

15. The system for producing algae of claim 1, wherein water used for the growth media is reclaimed water.

16. The system for producing algae of claim 1 comprising a water reclamation system comprising a particulate filter to filter particulate matter from used growth media, a UV light source to kill living organisms, a reverse osmosis membrane, and gaseous ozone, wherein used growth media is cleaned and resulting cleaned water is utilized as a component of new growth media.

17. The system for producing algae of claim 1 further comprising a centrifuge connected to the production tank, wherein the algae in the growth media is introduced into the centrifuge to substantially separate the algae from the growth media.

18. The system for producing algae of claim 1 wherein the beads comprise sodium alginate.

19. The system for producing algae of claim 1 wherein the beads comprise a pH buffering agent.

20. A system for producing algae comprising:
an algae production tank having algae growth media therein; a visible light source located inside the production tank, the light capable of being submerged in the growth media;
a rotating blade proximate a bottom portion of the production tank for the purpose of mixing the growth media;
a diffuser inside the production tank proximate the bottom portion;
an air chiller that introduces chilled and filtered air through the diffuser and into the growth media to chill and aerate the media; and
an incubation tank for producing culture attached proximate a top of the production tank, the incubation tank defining an opening whereby contents of the incubation tank can pass therethrough to the production tank; and,
wherein the system further comprises a plurality of beads in the growth media to limit algae growth on interior surfaces of the tank, light and blade and to provide accelerated algae growth, wherein the beads are porous to promote algae growth within the beads, and wherein at least one panel of the bead is configured to have at least one concave surface so that current from the mixing of the growth media does not result in a repeating angle of deflection of the beads.

21. The system for producing algae of claim 20 further comprising a particulate filter to filter particulate matter from used growth media, a UV light source to kill living organisms, a reverse osmosis membrane, and gaseous ozone, wherein used growth media is cleaned.

* * * * *